United States Patent [19]

Eton et al.

[11] Patent Number: 5,624,430

[45] Date of Patent: Apr. 29, 1997

[54] MAGNETIC DEVICE TO ASSIST TRANSCORPOREAL GUIDEWIRE PLACEMENT

[76] Inventors: Darwin Eton, 822 N. East Ave., Oak Park, Ill. 60302; Richard Torti, 9 Maud Graham Cir., Burlington, Mass. 01803; Vijay Gondhalekar, 357 Commercial St., #501, Boston, Mass. 02109

[21] Appl. No.: 345,939

[22] Filed: Nov. 28, 1994

[51] Int. Cl.$^6$ .................................................. A61B 17/00
[52] U.S. Cl. ............................................. 606/1; 128/772
[58] Field of Search ..................... 128/772; 600/11, 600/12; 606/106, 1

[56] References Cited

U.S. PATENT DOCUMENTS

| | | | |
|---|---|---|---|
| 4,244,362 | 1/1981 | Anderson | 128/200.26 |
| 4,913,139 | 4/1990 | Ballew | 128/200.11 |
| 5,096,763 | 3/1992 | Ogata et al. | 600/12 X |
| 5,171,233 | 12/1992 | Amplatz et al. | 604/281 |
| 5,269,759 | 12/1993 | Hernandez et al. | 604/96 |
| 5,342,371 | 8/1994 | Welter et al. | 606/113 |

OTHER PUBLICATIONS

Stent Placement for Iliac Artery Occlusions: Modified "Wire-Loop" Technique with Use of the Goose Neck Loop Snare.
Gordon K. McLean, Saruhan Cekirge, Jeffrey P. Weiss, Richard G. Foster. Technical Developments and Instrumentation, 1994 vol. 5, No. 5.
Ferruci JT, Mueller PR Interventional radiology of the biliary tract, Gasteroenterology 1982;82:974.
Ring EJ, Kerlan RK Interventional biliary radiology. AJR 1984:142:31.
McPhearson GAD, Benjamin IS, Hodgson HJF, Bowley NB, Allison DJ, Blumgart LH.
Pre-operative percutaneous transhepatic biliary drainage: the results of a controlled trail. Br J Surg 1984;71:371.
Schwarz W, Rosen RJ, Fitts WR Jr, et al. Percutaneous transhepatic drainage preoperatively for for benign strictures. Surg Gynecol Obstet 1981;137:613.
Finney RP Double-J and diversion stents. Urol Clin North Am. 1982:9:89.
Miller RP, Reinke DB, Clayman RV, Lange PH Percutaneous approach to the ureter. Urol Clin North Am 1982:9:31.
Segura JW, Patterson DE, LeRoy AJ:. et al. Percutaneous removal of kidney stones: review 1000 cases. J Urol 1985;134:1077.
Smith AD, Orihuela E, Crowley AR Percutaneous management of the pelvic tumors: a treatment option in selected cases. J Urol 1987;137:852.

Primary Examiner—Michael Powell Buiz
Assistant Examiner—Patrick W. Rasche
Attorney, Agent, or Firm—Peter J. Manus, Esq.

[57] ABSTRACT

Devices and methods are described to facilitate the coupling of two wires introduced into the vascular system at two different points in the body. The coupling enables the formation of a continuous wire entering the body at one point and exiting at another remote point. The device consists of two wires "A" and "B" with a magnetic element attached to one end of each wire. The coupling is formed by the forces of attraction between the magnetic elements. Wire "A" is introduced at one point in the vascular system, for example, in the femoral artery. Wire "B" is then introduced at another point in the vascular system, for example, the axiliary artery. The wires are advanced towards each other under fluoroscopic guidance. The magnetic tips couple once the two wires near each other. The coupled wires are then withdrawn together from either of the two access sites. Once the magnetic coupling exits the body, a single wire is left traversing the vascular system. This wire can then serve as a monorail over which to exchange catheters, transport tools and implants and to perform procedures. This device will facilitate the development of bi-directional endovascular, biliary, genito-urinary and gastro-intestinal procedures. The applications of this device are not limited to human subjects.

15 Claims, 2 Drawing Sheets

LEGEND:
N ⟵⟶ END POLARIZED "NORTH"
S ⟵⟶ END POLARIZED "SOUTH"

LEGEND:
N ⟵⟶ END POLARIZED "NORTH"
S ⟵⟶ END POLARIZED "SOUTH"

LEGEND:
N ⟵⟶ END POLARIZED "NORTH"
S ⟵⟶ END POLARIZED "SOUTH"

MAGNETIC DEVICE TO ASSIST TRANSCORPOREAL GUIDEWIRE PLACEMENT

TECHNICAL FIELD

This invention relates to devices used in surgery and, in particular, endovascular, genito-urinary, hepato-biliary, and gastro-intestinal surgery.

BACKGROUND—FIELD OF INVENTION

Historically, vascular procedures have been performed using open surgical techniques requiring extensive incisions and operating room time. As instruments became miniaturized, a variety of other therapeutic options have arisen. Examples include: balloon angioplasty, atherectomy, stent placement, laser ablation, stent graft placement, intraluminal ultrasound, and angioscopy. Guidewires have had a place in all of these applications. The guidewires serve as a conduit in the vascular circulation for the introduction of catheters, cutting devices, fiber optics, and ultrasound probes. Additionally, similar advances have been made in the hepato-biliary tree[4,5,6,7], the genito-urinary [8,9,10,11] and the gastro-intestinal systems for treatment of tumors and other obstructive lesions.

Occasionally, the need has arisen to perform a therapeutic intervention from two ends of the effected site in the vascular system. This has required passing a guidewire from two access points[1]. Presently, a guidewire is introduced from one access point and the distal end is physically grasped and pulled across the vascular system by a device such as the snare type probe[2] inserted at a second site. The procedure to grasp the distal end is time consuming and requires dexterity on the part of the physician performing the procedure. The lengthy visualization by means of a fluoroscope, necessary to carry out this procedure, exposes the patient to dosages of X-ray radiation which would otherwise be unnecessary. The device we describe in this patent shortens the time and greatly facilitates the procedure for placing a single guidewire, or a monorail, which traverses the vascular system from one access site to another.

BACKGROUND—DISCUSSION OF PRIOR ART

The prior art relates to devices and techniques used for retrieving broken pieces of catheters and other foreign objects from within the vascular system of a patient[2,3]. The same devices are occasionally used for grasping the distal end of a guidewire and pulling it through the vascular tree to establish a guidewire which enters at one access point and exits at another. Although these devices perform very well for retrieving foreign objects from within the patient they are not designed for easily and efficiently placing a guidewire which traverses the vascular system between two access sites.

One of such devices utilized for grasping the distal end of a guidewire inserted into the vascular tree consists of a distal loop or snare. The snare-type probe is used to retrieve broken catheters as well as to pull guidewires through the vascular tree. The snare is described in U.S. Pat. No. 05,171,233 issued to Amplatz, Kurt et al[2]. The physician introduces a guidewire at one access site and advances it up to a point along the vascular tree. The snare type probe is introduced at a second access point and the physician positions the snare over the distal end of the guidewire and tightens the said snare to grasp the guidewire end. The secured distal end of the guidewire now has a transverse orientation with respect to the axis of the snare-type probe. The guidewire end is now pulled through the vessels of the vascular system out of the second access site. The transversely orientated end of the guidewire may potentially traumatize the blood vessel walls during its passage through the vascular system of the patient. Alternately, the snare together with the secured distal end of the guidewire is pulled into a sheath and the sheath is subsequently withdrawn from the vascular system thus pulling the guidewire with it.

One of the reported problems with the snare-type probe is that the snare wire can be easily kinked during engagement of the distal end of the guidewire[3]. As a result the snare is rendered ineffective and is required to be replaced.

The procedure for placing and tightening the snare requires considerable maneuvering of the distal end by manipulation of the proximal end of the probe. It is a time consuming process. The visualization necessary to carry out the positioning maneuvers is with the aid of a fluoroscope. The time spent in maneuvering the snare to grasp the end of the guidewire results in unnecessary long exposure of the patient to X-ray radiation from the fluoroscope.

Another device utilized for extracting foreign objects from a patient's body as well as grasping the distal end of a guidewire inserted into the vascular tree, is described in U.S. Pat. No. 05,342,371 issued to Lawrence H. Welter et al[3]. It uses a helical snare to perform the function of extracting foreign objects from a patient's body. The helical snare is of a relatively intricate construction made up of a hollow tubular member with a filament wire wrapped around the exterior of the distal end of the tubular member to form a helical snare loop. The filament wire is threaded through the tubular member to emerge at the proximal end of the said member. The filament end of the wire is manipulated to open or close the loop. The physician positions the helical snare loop over the distal end of the guidewire and tightens the loop to grasp the guidewire end which, as a consequence, lies snug along the body of the hollow tubular member. This is an advantage compared to the operation of the snare-type probe[2] as the grasped end of the guidewire does not lie transverse to the axis of the said tubular member thus reducing the potential for traumatizing the blood vessel walls during withdrawal through the vascular system of the patient.

The procedure for placing and tightening the helical snare loop over the guidewire requires considerable maneuvering and manipulation. It is a time consuming process. The visualization necessary to carry out the positioning maneuvers is with the aid of a fluoroscope. The time spent in maneuvering the helical snare loop to engage the end of the guidewire results in unnecessary long exposure of the patient to X-ray radiation from the fluoroscope.

REFERENCES (1) Stent Placement for Iliac Artery Occlusions: Modified "Wire-Loop" Technique with Use of the Goose Neck Loop Snare. Gordon K. McLean, Saruhan Cekirge, Jeffery P. Weiss, Richard G. Foster. Technical Developments and Instrumentation, 1994 Volume 5, Number 5

(2) Snare-type probe. U.S. Pat. No. 05,171,233 Inventors: Amplatz, Kurt. Kotula, Frank. Mazzochi, Rudy. Assignee: Microvena Corp. Vadnais Heights, Minn.

(3) Helical surgical snare. U.S. Pat. No. 05,342,371 Inventors: Walter, Lawrence H. Downey, Scott D. Hall, Todd A. Assignee: Cook Corporation, Bloomington, Ind.

(4) Ferruci J T. Mueller P R: Interventional radiology of the biliary tract, Gasteroenterology 1982; 82: 974

(5) Ring EJ, Kerian R K: Interventional biliary radiology. AJR 1984: 142: 31

(6) McPhearson G. A. D., Benjamin I. S., Hodgson H. J. F., Bowley N. B., Allison D. J., Blumgart LH: Pre-operative percutaneous transhepatic biliary drainage: the results of a controlled trial. Br J Surg 1984; 71: 371

(7) Schwarz W, Rosen R. J., Fills W. R. Jr, et at: Percutaneous transhepatic drainage preoperatively for for benign strictures. Surg Gynecol Obstet 1981; 137: 613

(8) Finney R. P., Double-J and diversion stents. Urol Clin North Am. 1982:9: 89

(9) Miller R. P., Reinke D. B., Clayman R. V., Lange P. H.: Percutaneous approach to the ureter. Urol Clin North Am 1982: 9: 31

(10) Segura J. W. Patterson D. E., LeRoy A. J. et al: Percutaneous removal of kidney stones: review 1000 cases. J Urol 1985; 134: 1077

(11) Smith A. D., Orihuela E, Crowley A. R.: Percutaneous management of the pelvic tumors: a treatment option in selected cases. J Urol 1987; 137: 852

SUMMARY OF THE INVENTION

The foregoing problems are solved and a technical advance is achieved through the invention described herein. The device offers a quick and easy means for placing a single guidewire which traverses the vascular system from one access site to another. This guidewire can then serve as a monorail over which to exchange catheters, transport tools and implants and to perform procedures.

The magnetic device constitutes a pair of wires with a magnetic element attached to one end of each wire. The size of the wires and the magnetic elements are such as to be suitable for entry into the vessels of interest. The magnetic element attached to each wire is polarized such that the axis of magnetic polarization of the said element is along the axis of the wire. Furthermore the polarization of the elements is such that when the free ends of the magnetic elements, namely the ends not attached to the guidewires, are brought together there is a force of attraction between them leading to a magnetic coupling. The magnetic elements can be formed from a permanent magnetic material, a ferromagnetic material or an electro-magnet. For placing a single wire which traverses the vascular system, one of the pair of the mamagnet elements with an attached wire is introduced into the said system at one access site. The second of the pair of the magnetic elements with an attached wire is introduced into the second access site. Both the magnetic elements are advanced towards each other by pushing on the proximal ends of the wires. When the magnetic elements approach to within a distance where the magnetic forces of attraction are sufficient to overcome restraining forces on the wires traversing the vessels, the magnetic elements move towards each other and join up. The coupling force is dictated by the strength of magnetization of the magnetic elements. The process for forming this coupling requires significantly less usage of the fluoroscope and less manipulation on the part of the physician. In tact the nature of the magnetic forces align the magnetic elements without external intervention. Once the coupling is formed, one of the wires is withdrawn causing the second coupled wire to be pulled all the way, in through one access site and out through the other thus traversing and forming a monorail across the vascular system. The savings in time, minimization of exposure to X-ray radiation and minimization of trauma to the vessels of the vascular system during this procedure are a distinctive feature of this invention.

The broader implications of the invention go beyond the vascular system. Presently, percutaneous intervention in the hepato-biliary tree, the urinary and the gastro-intestinal systems is, in the majority of cases, single sided, that is via one access site. This imposes the need to physically push devices, tools and implants from one access site, often through torturous pathways, up to the affected site. A quick and easy means of establishing a continuous guide way or monorail traversing the lesions to be treated from two access sites removes one of the barriers to developing new forms of two sided intervention. Physical access to the two ends of the monorail exiting the two access sites offers the physician the option of pushing or pulling devices, tools and implants into place and anchoring them in place more precisely than is possible via a single sided access. Moreover, the physical action of pulling as opposed to pushing is easier and less time consuming leading to reduced costs in the operating room. Lastly, the need of invasive guidance equipment such as a cystoscope or a gastro-intestinal or biliary endoscope may be obviated by the non invasive floroscope in the deployment of the monorail.

OBJECTS AND ADVANTAGES

Accordingly, the objects and advantages of this invention are to provide a simple construction.

to provide a self aligning feature of the coupling to provide quick and easy means for coupling wires inside the human body to provide a device with absence of rough surfaces or edges or projections to minimize trauma caused during withdrawal of wires to minimize exposure to X-ray radiation during coupling process Further objects and advantages of this invention will become apparent from a consideration of the drawings and ensuing description.

DETAILED DESCRIPTION OF THE INVENTION

Figure 1:
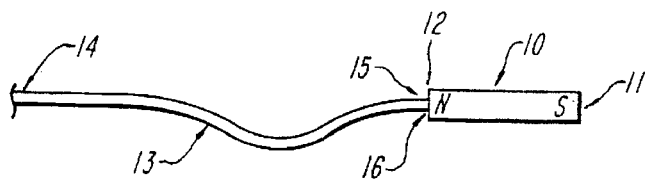
FIG. 1 is an illustrative example of a wire and magnetic element with the distal end of the magnet element having a "south" polarity. This wire and magnetic element combination is referred to as guidewire "A".
Figure 2:
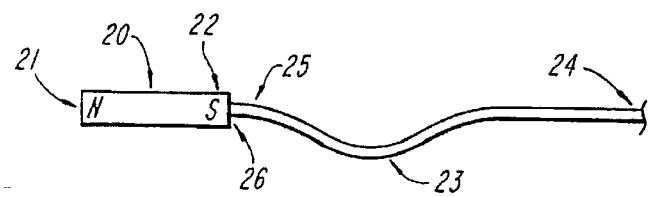
FIG. 2 is an illustrative example of a wire and magnetic element with the distal end of the magnet element having a "north polarity". This wire and magnetic element combination is referred to as guidewire "B".

The invention is described with reference to FIGS. 1 and 2. FIG. 1 shows a wire "A" 13 with a magnetic element "A" 10 attached to one end of the said wire. The distal end 15 of wire "A" is attached to the proximal end 12 of the magnetic element "A" 10. The magnetic element "A" 10 is attached to the distal end 15 of wire "A" at 16 by any suitable means such as brazing, soldering, snap on attachment, screw on attachment or a strong epoxy bond. The magnetic element "A" 10 is polarized such that the proximal end 12 of the said magnetic element has a north polarity and the distal end 11 has a south polarity. FIG. 2 shows a wire "B" with a magnetic element "B" 20 attached to one end of the said wire. The distal end 25 of wire "B" is attached to the proximal end 22 of the magnetic element "B"20. The magnetic element "B" 20 is attached to the distal end 25 of wire "B" at 26 by any suitable means such as brazing, soldering, snap on attachment, screw on attachment or a strong epoxy bond. The magnetic element "B" 20 is polarized such that the proximal end 22 of the said magnetic element has a south polarity and the distal end 21 has a north polarity. The magnetic elements "A" 10 and "B" 20 may be coated with a material compatible with usage in the human body. The coating, if present, may serve to add mechanical strength to the surface of the magnet so as to prevent the material from chipping or flaking. The wires themselves may be of any suitable material such as stainless steel. The proximal ends of the wires 13 and 23 are identified with reference numbers 14 and 24, respectively.

Figure 3:
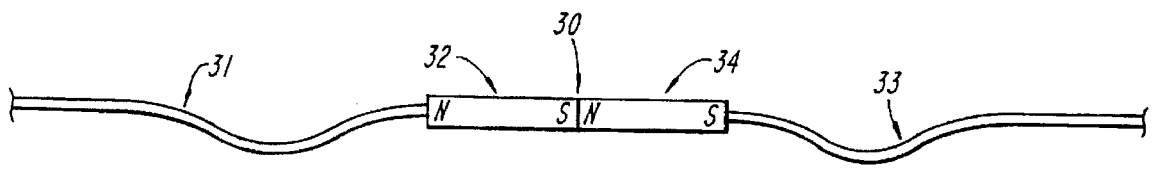
FIG. 3 is an illustrative example of the relative orientation of guidewires "A" and "B", as shown in FIG. 1 and FIG. 2, when they form a magnetic coupling.
Figure 4:
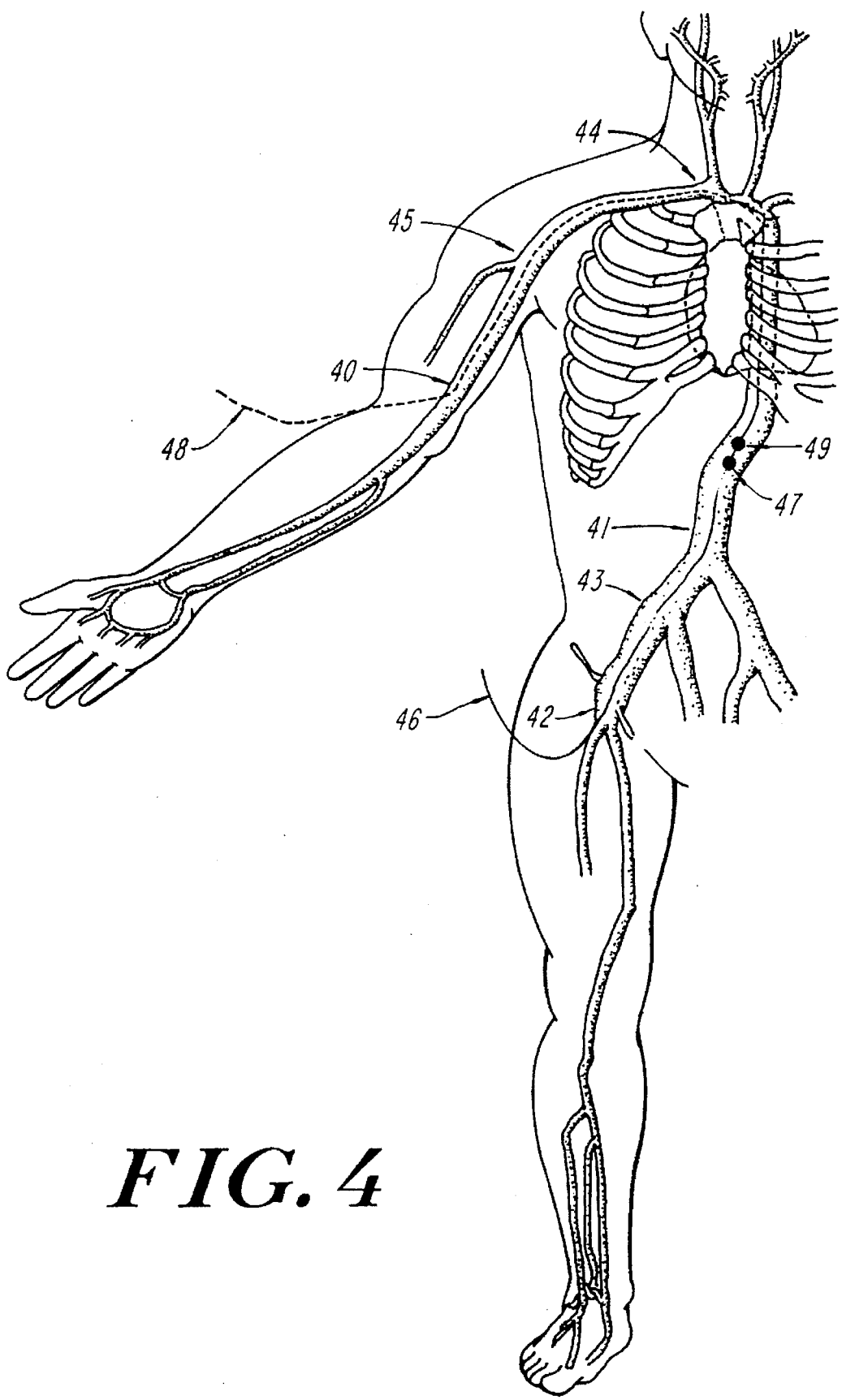
FIG. 4 shows an illustrative example of the deployment of the invention in the human vascular system.

The operation of the invention is described with reference to FIG. 3 and the human vascular system part of which is shown in FIG. 4. When the wire "A" 31 with the attached magnetic element "A" 32 and wire "B" 33 with the attached magnetic element "B" 34 are brought into close proximity, the said magnetic elements attract each other. The magnetic force of attraction hold the said magnetic elements together. The forces are such as to align the said magnetic elements along their respective axis. The magnetic coupling 30 thus formed is self aligning. The forces of attraction between the said magnetic elements and the resulting self aligning feature eliminates the need for any manipulation to from a coupling as with the snare-type probes[2,3]. The simplicity and ease with which the said magnets couple togather is a significant factor in reducing the time and the exposure to X-ray radiation which is otherwise necessary to form a continuous guide way.

An illustrative example of the use of the invention is described with reference to FIG. 4 which shows part of the human vascular system relevant to the description. In order to establish a continuous guide path along the length of the Aorta 41 in the region below the heart, the leading end of guidewire "A" 46 is introduced into the right Femoral artery 42 and pushed towards the Aorta 41. Guidewire "B" 48 is introduced into the right Subclavian artery 44 via an Arteriostomy in the right axiliary 45 or Brachial artery 40 and pushed towards the heart and into the Aorta 41. The two guidewires "A" 46 and "B" 48 are manoeuvred towards each other to a point where the magnetic elements "A" 47 and "B" 49 at the distal ends of the said guidewires experience forces of attraction such as to align themselves and eventually form a coupling. An implant or tool may now be effortlessly transported along this continuous guide path either by slipping it concentrically around the said guidewires or by exchanging the said guidewires over an exchange catheter and introducing the device through the catheter. Also, the device may be slipped non-concentrically but parallel to the said wires. Once a continuous guide path is established, pulling or pushing of the interventional device becomes possible. Additionally, monitoring diagnostic procedures using angioscopy or intraluminal ultrasound from one end are facilitated during an interventional procedure at the other end.

The configuration of two access points in the human body bridged by an interconnecting monorail increases the options available to the surgeon or interventionalist. It is analogous to operating with two hands instead of one. The device proposed herein facilitates creating this configuration.

The human vascular system, used here as an example to illustrate the operation of the invention, by no means limits the utility of the invention to the human vascular system.

While the present invention is described above in considerable particularity, it is to be understood that those of ordinary skill in the art may be able to make certain modifications to, or deletions from, the specific embodiments described herein, without departing from the spirit or the scope of the inventions, as set forth in the appended claims.

We claim:

1. A magnetic device for establishing a continuous guide way in a system of interconnected body vessels, organs, and passages in tissue where the magnetic device enters the system at a first access site and exits the system at a second access site remote from the first access site, comprising:
   (a) a pair of thin wires sized for insertion into the system and each having a distal end and a proximal end, said wires being of sufficient length to traverse the system,
   (b) a pair of elongate magnetic elements sized and configured for axial insertion into the system, each of said magnetic elements having a distal end and a proximal end,
   (c) means for attaching said distal end of each of said pair of wires to the proximal end of one of said pair of magnetic elements of a first polarity, and means for attaching said distal end of the second of said pair of wires to said proximal end of the second of said pair of magnetic elements of a second polarity opposite to that of said first polarity, said proximal ends of said pair of wires being free and said distal ends of the said pair of magnetic elements being free, whereby said free distal ends of said pair of magnetic elements are drawn into an axially self-aligning, magnetic element end-to-magnetic element end coupling connection when said distal ends of said magnetic elements are near one another in the system, said coupling connection and said magnetic elements individually being sized and configured for movement in narrow and curved portions of said interconnected body vessels, organs and passages and the magnetic axis of each one of said magnetic elements being aligned with (i) the axis of the portion of said wire attached to said one magnetic element and (ii) with the magnetic axis of the other one of said magnetic elements when they are coupled.

2. The device of claim 1, where the device is used for establishing a continuous guide way in the vascular system of a patient.

3. The device of claim 1, where the device is used for establishing a continuous guide way in the hepato-biliary system of a patient.

4. The device of claim 1, where the device is used for establishing a continuous guide way in the urinary system of a patient.

5. The device of claim 1, where the device is used for establishing a continuous guide way in the gastro-intestinal system of a patient.

6. The device of claim 1, wherein both of said pair of magnetic elements are made of permanent magnet material.

7. The device of claim 1, wherein both of said pair of magnetic elements are electromagnets.

8. The device of claim 1, wherein one magnetic element of said pair of magnetic elements is made of permanent magnetic material, and the second magnetic element of said pair of magnetic elements is made of ferromagnetic material.

9. The device of claim 1, wherein one magnetic element of said pair of magnetic elements is an electromagnet, and the second magnetic element of said pair of magnetic elements is made of ferromagnetic material.

10. The device of claim 1, wherein one magnetic element of said pair of magnetic elements is an electromagnet, and the second magnetic element of said pair of magnetic elements is made of ferromagnetic material.

11. A method for establishing a continuous guide way between two remote sites of entry in a system of body vessels organs, and passages in tissue comprising of the following steps:

(a) providing a pair of wires each with distal and proximal ends and a pair of elongate magnetic elements each with distal and proximal ends where each of said magnetic elements is secured at its proximal end to a distal end of an associated one of the wires, (b) attaching said proximal ends of said magnetic elements to said distal ends of adjacent portions of said wires at their distal ends with the magnetic axes of said magnetic elements aligned with said axes of said adjacent wire portion and oriented with said distal ends of said magnetic elements having an opposite polarity.

(c) introducing at an access site into the system the distal end of one of the magnetic elements and the distal end of said associated wire, (d) introducing at a second access site into the system the distal end of the second of said magnetic elements and the distal end of said associated wire, (e) advancing along the system each of the magnetic elements by pushing on the proximal ends of the respective attached wire, (f) advancing the magnetic element in the system in the prescribed manner described in (e) till the magnetic elements approach each other, (g) allowing the magnetic elements to magnetically couple to each other axially, magnetic element end-to-magnetic element en with the magnetic forces of attraction holding the two said magnetic elements together to form a continuous guide way between the two access sites, with the proximal ends of the wires extending out of the access sites, and with the magnetic axes of said magnetic elements, when coupled, being mutually aligned.

12. The method of claim 11, where the method is used for establishing a continuous guide way in the vascular system of a patient.

13. The method of claim 11, where the method is used for establishing a continuous guide way in the hepato-biliary system of a patient.

14. The method of claim 11, where the method is used for establishing a continuous guide way in the urinary system of a patient.

15. The method of claim 11, where the method is used for establishing a continuous guide way in the gastro-intestinal system of a patient.

* * * * *